US010197543B1

(12) United States Patent
Slaugh et al.

(10) Patent No.: US 10,197,543 B1
(45) Date of Patent: Feb. 5, 2019

(54) METHOD FOR THE PRODUCTION OF A VERIFIED ENRICHED SHELL EGG

(71) Applicants: Bart T. Slaugh, Jeffersonville, PA (US); Simon M. Shane, Durham, NC (US)

(72) Inventors: Bart T. Slaugh, Jeffersonville, PA (US); Simon M. Shane, Durham, NC (US)

(73) Assignee: Eggland's Best, Inc., Jeffersonville, PA (US)

( * ) Notice: Subject to any disclaimer, the term of this patent is extended or adjusted under 35 U.S.C. 154(b) by 1001 days.

(21) Appl. No.: 14/250,774

(22) Filed: Apr. 11, 2014

Related U.S. Application Data

(60) Provisional application No. 61/919,425, filed on Dec. 20, 2013.

(51) Int. Cl.

| | |
|---|---|
| ***A23K 1/17*** | (2006.01) |
| ***G01N 33/08*** | (2006.01) |
| ***A23L 1/32*** | (2006.01) |
| ***A61K 39/112*** | (2006.01) |
| ***G01N 33/82*** | (2006.01) |
| ***G01N 33/92*** | (2006.01) |
| ***G01N 33/569*** | (2006.01) |
| *A61K 39/00* | (2006.01) |

(52) U.S. Cl.
CPC ................ *G01N 33/08* (2013.01); *A23L 1/32* (2013.01); *A61K 39/0275* (2013.01); *G01N 33/56916* (2013.01); *G01N 33/82* (2013.01); *G01N 33/92* (2013.01); *A23V 2002/00* (2013.01); *A61K 2039/522* (2013.01); *A61K 2039/552* (2013.01); *G01N 2469/20* (2013.01)

(58) Field of Classification Search
CPC ...................................................... G01N 33/08
See application file for complete search history.

(56) References Cited

U.S. PATENT DOCUMENTS

| | | | | |
|---|---|---|---|---|
| 5,246,717 | A | 9/1993 | Garwin | |
| 5,897,890 | A | 4/1999 | Schneideler | |
| 6,436,451 | B1 | 8/2002 | Slaugh | |
| 6,805,886 | B2 | 10/2004 | Slaugh | |
| 7,470,439 | B1 | 12/2008 | Nizio | |
| 7,533,490 | B2 | 5/2009 | Kerkhoff | |
| 7,603,284 | B2 | 10/2009 | Stroman | |
| 7,681,527 | B2 | 3/2010 | Pratt | |
| 7,806,079 | B2 | 10/2010 | Liou | |
| 7,810,451 | B2 | 10/2010 | Pratt | |
| 7,836,631 | B2 | 11/2010 | Kerkhoff | |
| 7,836,850 | B2 | 11/2010 | Pratt | |
| 7,974,881 | B2 | 7/2011 | Culver | |
| 8,019,633 | B2 | 9/2011 | Stroman | |
| 8,037,846 | B2 | 10/2011 | Pratt | |
| 8,256,381 | B2 | 9/2012 | Pratt | |
| 8,433,593 | B2 | 4/2013 | Stroman | |
| 8,505,488 | B2 | 8/2013 | Pratt | |
| 2009/0047378 | A1 * | 2/2009 | Stewart ................ | A23K 20/158 426/2 |
| 2012/0016814 | A1 | 1/2012 | Evans | |

OTHER PUBLICATIONS

Burley, Johnson, "Market survey of quality and freshness of eggs produced under an enhanced hen nutrition and egg production program", Journal of Applied Poultry Research, published Dec. 1, 2013.

Author Unknown, "BioChek Salmonella SE/ST Antibody Kit", http://egg-cite.com/articles/single.aspx?contentID=948, Jan. 10, 2012.

* cited by examiner

*Primary Examiner* — Albert M Navarro

(74) *Attorney, Agent, or Firm* — Muskin and Farmer LLC

(57) ABSTRACT

A method, apparatus and computer readable storage medium for producing a verified enriched shell egg (VESE) and the resulting VESE therefrom can comprise a method of production and verification. The method of production and verification can ensure that the VESE has a reduced risk of presence of *Salmonella enteritidis*, has high desirable nutrient contents, low undesirable nutrient contents, and good egg and shell qualities. Additionally, a method of tracking the VESE throughout the entire process can be included, as well as a method for indicating an egg has been produced as part of the VESE method.

5 Claims, 9 Drawing Sheets

METHOD FOR THE PRODUCTION OF A VERIFIED ENRICHED SHELL EGG

CROSS REFERENCE TO RELATED APPLICATIONS

This application claims benefit to provisional patent application No. 61/919,425 filed Dec. 20, 2013, which is incorporated by reference herein in its entirety.

FIELD OF THE INVENTION

The present inventive concept relates to a verified, enriched shell egg (VESE) that is produced through a specific method and verification process such that the VESE comprises a minimum level of specific nutritional contents and is free of *Salmonella Enteritidis* (SE) contamination.

BACKGROUND

In the U.S., the typical egg is produced according to the Food and Drug Administration's (FDA's) guidelines for limiting *Salmonella Enteritidis* (SE) contamination. However, these parameters are not always sufficient to eliminate the possibility of contamination. Over 6.95 billion table eggs were produced in August 2013 in the United States. Given the large number of eggs consumed, it is likely under the current standards that eggs that are infected with SE will reach the consumer. Illness caused by the consumption of SE-contaminated eggs is a serious public health problem. The effects caused by SE infection may include mild to severe gastrointestinal illness, short term or chronic arthritis, and even death in some cases.

The current FDA procedures comprise requirements relating to pullets, biosecurity, pest and rodent control, cleaning and disinfection, storage, environmental testing and egg testing. Pullets must be raised under monitored conditions, with their environment tested for SE when the pullets are 14-16 weeks old, if this test is negative, a second test is conducted at 40-45 weeks of age and additional environmental tests are conducted 4-6 weeks after the end of each molt. If any of the environmental tests are positive, environmental cleaning and disinfection must be performed, and egg testing for SE must be conducted within two weeks of the start of laying. However, egg testing is not routinely conducted, but is required only if an environmental test is positive. This egg testing is conducted according to a specified schedule and eggs that were produced by a flock that had tested positive can be allowed to enter the market if a sufficient number of egg tests come back negative of SE contamination. Egg testing is conducted according to Chapter 5 of FDA's *Bacteriological Analytical Manual*, December 2007 edition, or a method that is equivalent in accuracy, precision, and sensitivity in detecting SE contamination.

The FDA provides suggestions and requirements for biosecurity measures that should be taken to prevent the introduction or transfer of SE into or among poultry houses. The minimum requirements include addressing cross-contamination from equipment and people moving among poultry houses. Additionally, the number of visitors to the farms should be limited and actions should be taken to prevent stray animals from accessing poultry houses.

Pest control is conducted by monitoring for rodents and flies, and taking appropriate action to achieve a satisfactory level of control. Additionally, debris and vegetation should be removed from within and outside of poultry houses. Cleaning and disinfection of a poultry house is only required if the environmental or egg testing revealed a positive test at any point in the life of the flock. Storage and transportation must be performed at temperatures at or below 45 degrees F. beginning 36 hours after time of lay.

These required processes are sufficient to provide an egg product that has a limited possibility of contamination. However, this process may allow a significant number of SE contaminated eggs to reach the end consumer.

In addition to concerns about SE contamination, there are other components of eggs that make them less desirable to consumers. These less desirable components include saturated fat, which is considered to have negative effects on cardiovascular health, which negatively impacts the consumption of eggs. The reduced consumption of eggs prevents people from obtaining many of the beneficial contents present in eggs, such as protein and numerous other nutrients. However, an egg's beneficial nutrients can be increased through specific supplements added to the feed consumed by the chickens. By increasing the amount of beneficial nutrients in an egg, the negative perception concerning egg contents may be overcome and greater benefits from consuming eggs may be realized.

The beneficial nutrients that can be increased in eggs include vitamins D and E, as well as Omega-3 fatty acids. Omega-3s are generally recognized for their ability to reduce triglycerides in the blood and lower blood pressure. Additionally, the consumption of omega-3s may be able to counteract some of the negative cardiovascular effects of saturated fats. However, most individuals in the United States do not consume a sufficient amount of Omega-3 fatty acids. Additional consumption of Omega-3 rich food sources, such as eggs, could possibly result in improved health of individuals. What is needed is a VESE that comprises vitamins and nutrients that have been shown to have beneficial health effects, such as vitamins E and D, and Omega-3 fatty acids, as well a reduced amount of saturated fat.

Certain characteristics regarding the physical properties of an egg also impact the consumers' perception of egg quality. The USDA grades the quality of an egg according to interior and exterior qualities, after which they are sorted by weight. Eggs can be graded AA, A or B quality, with AA being the highest quality and B the lowest.

Interior egg quality is graded by candling and breakout evaluation expressed by Haugh units. The interior quality is dependent on the properties exhibited by the albumen, yolk and air cell. The albumen is judged on the basis of clarity and thickness, with higher Haugh units assigned to eggs with a thicker albumen. Yolk quality is dependent upon the distinctness of its outline, size, shape, and absence of defects. Higher grade eggs have shallower air cells.

The exterior of the egg is examined for cleanliness, soundness, texture and shape. Shells cannot be broken, cracked or appear unsound. The ideal egg shape is oval, with one end slightly larger than the other end. Eggs with abnormal shells, including misshapen, poor textured, ridged, thin, or rough shells are classified as grade B.

Due to the USDA grading system and the consumer perception of less than desirable physical properties, it is important that any egg produced have desirable properties. Studies have shown that many of these physical properties, such as shell strength, yolk color and albumen height can be controlled through supplements provided in the diet of the laying hen and management practices applied to the flocks.

In order to ensure that an egg reaching the final consumer has been made according to the use of a particular process and all criteria set forth in the process have been met, each component of the process must be documented. Additionally, each egg must be traceable along every step of the process. Finally, marking on the egg must provide some notification to the consumer that it was produced under a strict set of conditions.

What is needed is a method of egg production and verification, which comprises processes that can significantly reduce the possibility that a egg contaminated with SE will reach consumers, increase the nutritional content and physical properties of the egg, reduce less desirable nutritional attributes of the egg, and identifies the egg as having these characteristics.

SUMMARY OF THE INVENTION

An aspect of the present method is to provide a method of egg production and verification, which comprises processes that can significantly reduce the possibility that a egg contaminated with SE will reach consumers, increase the nutritional content and physical properties of the egg, reduce less desirable nutritional attributes of the egg, and identifies the egg as having these characteristics.

The above aspect can be achieved by a method for producing a verified enriched shell egg comprising: providing a chicken from a flock; providing a feed supplement mix comprising a vitamin D supplement and a vitamin E supplement; mixing the feed supplement mix with a feed mixture comprising canola oil to create a feed product; performing an assay to verify the vitamin D, vitamin E, saturated fats and Omega-3 fatty acid levels in the feed product; performing an assay to verify that the final feed product is free from antibiotics, proteins from bovine sources, and pesticides; feeding the final feed product to the chicken; obtaining a first egg from the chicken; testing the first egg for an acceptable level of vitamin D, vitamin E, saturated fat and Omega-3 fatty acids; and obtaining a second egg from the chicken if the levels of vitamin D, vitamin E, saturated fat and Omega-3 fatty acids in the first egg were within acceptable limits.

Additionally, the above aspects can also be achieved by a method for producing a verified enriched shell egg comprising: providing a chicken; vaccinating the chicken with a *Salmonella typhimurium* live attenuated mutant vaccine when the chicken is less than 48 hours old; vaccinating the chicken with the *Salmonella typhimurium* live attenuated mutant vaccine when the chicken is between the ages of 14 days and 21 days; vaccinating the chicken with a *Salmonella enteritidis* multi-phage type, inactivated oil emulsion vaccine when the chicken is between the ages of 12 weeks and 14 weeks; performing an environmental test for *Salmonella enteritidis* contamination of a chick box liner used to house the chicken; performing an environmental test for *Salmonella enteritidis* contamination of a laying house housing the chicken when the chicken is 14 weeks old and when the chicken is 40-45 weeks old; providing a feed supplement mix comprising a vitamin D supplement and a vitamin E supplement; mixing the feed supplement mix with a feed mixture comprising canola oil to create a feed product; performing an assay on the feed product to verify the vitamin D, vitamin E, saturated fats and Omega-3 fatty acid levels in the feed product; performing an assay on the feed product to verify that the final feed product is free from antibiotics, proteins of bovine sources and pesticides; feeding the final feed product to the chicken; obtaining a first egg from the chicken; testing the first egg for vitamin D, vitamin E, saturated fat and Omega-3 fatty acids; testing the first egg for *Salmonella enteritidis* antibodies; and; and obtaining a second egg from the chicken if the levels of vitamin D, vitamin E, saturated fat and Omega-3 fatty acids in the first egg were within acceptable limits and *Salmonella enteritidis* antibodies were present in the first egg.

BRIEF DESCRIPTION OF THE DRAWINGS

Further features and advantages of the present product and method, and various embodiments of the present product and method will become apparent and more readily appreciated from the following description of the preferred embodiments, taken in conjunction with the accompanying drawings of which.

DETAILED DESCRIPTION

The present production and verification method for producing a VESE can comprise numerous steps to ensure that the final product has all the desired elements, and little or none of the undesired elements. These steps provide the method of production, as well as methods for verification. If an egg is not produced according to the method of production, or if it fails one of the verification tests, it cannot be categorized as a VESE. A VESE produced from the present production and verification process can meet various criteria, making it more desirable and safer to consume than a generic egg produced to comply with minimum statutory requirements.

Specifically, the present production process includes steps that can reduce the risk of any possible contamination from SE, optimize egg quality, and enhance nutrient contents. Following all of the production steps can result in a uniform egg of high quality and excellent nutritional content that is free from SE contamination. However, to ensure that the VESE uniformly comprises these characteristics, verification tests on the eggs can also be implemented at various steps in the production process. Labeling and tracing mechanisms can be implemented so that if any verification tests do not meet the minimum requirements, the affected eggs or all chickens in the flock that produced the affected eggs can be isolated and not used as part of the system producing VESEs. The present production and verification process can be broken into separate co-existing smaller production and verification processes, which can address each of the beneficial elements of the VESE. These smaller production and verification processes can include, ensuring the eggs are free from SE contamination, ensuring the nutrient content and egg quality of the eggs, a system of tracking the flocks and eggs associated with the system and a method identifying VESEs to the consumer.

Production Methods and Verification to Eliminate SE Contamination

To control SE contamination, specific production steps can be taken throughout the rearing, laying, storage and transport processes, which when performed properly can significantly reduce the risk of SE contamination in the VESE. Additionally, consistent verification and testing methods can be utilized throughout the process to ensure that the production steps are actually being carried out and confirm that SE contamination of the VESEs is significantly reduced. This production and verification process can provide a final egg product that is much less likely to contain SE contamination than that provided by current statutory regulations.

Figure 1:
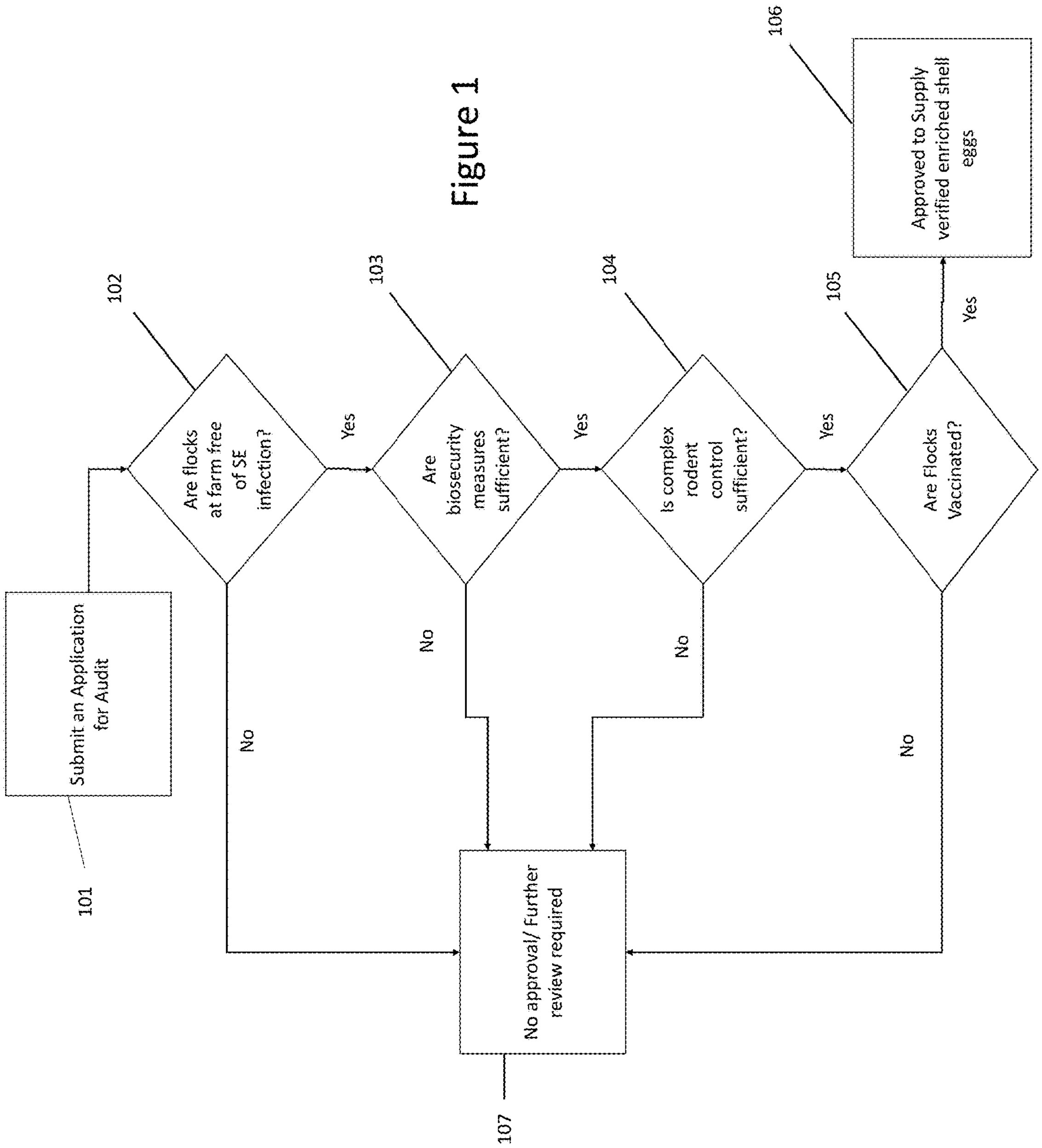
FIG. 1 is a flow chart showing the steps necessary for a farm to be approved for producing elements of the method to produce a VESE, according to an embodiment.

FIG. 1 is a flow chart showing the steps required prior to a farm being approved to produce elements of the method to produce a VESE, according to an embodiment. Prior to a farm or complex being allowed to produce a VESE, it can be subject to an approval process that can include a pre-production audit. This audit can review the SE status of all flocks on the farm to confirm freedom from infection, the biosecurity of the complex, the efficacy of rodent control and records of flock vaccination. A complex can submit an electronic or paper application 101 to be a producer of VESEs to a company, which approves the complex and the pre-production audit by this company can occur. The pre-production audit can check to ensure that the complex is meeting the minimum requirements to produce VESEs as specified in this document.

The flocks housed at the complex can be required to be free from SE infection 102. Once freedom from SE infection is demonstrated, the biosecurity measures to keep the facility free from SE contamination can be shown 103. The required biosecurity measures can be in accordance with SE-prevention Program as mandated by the FDA. A separate approval for rodent control methods can be required 104. As an additional assurance that the complex will be producing eggs that are free from SE contamination, a flock vaccination history, which confirms the administration of the vaccination schedule as described below can be required 105. If each of these requirements are met the complex can be approved to supply VESEs 106. If any one of these criteria are not met, the complex's application can be refused 107.

Flock Vaccination

Figure 2:
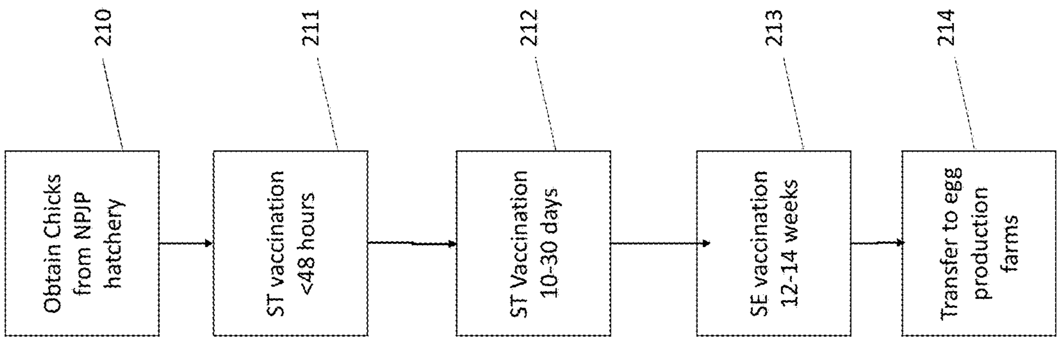
FIG. 2 is a flow chart showing the vaccination schedule for chicks intended for egg laying according to an embodiment.

FIG. 2 is a flow chart showing the vaccination schedule for chicks intended for egg laying according to an embodiment. Chicks can be obtained from a National Poultry Improvement Plan (NPIP) certified hatchery 210. The NPIP is an industry-state-federal program for the improvement of poultry and poultry products and has active controls of programs for reducing *Salmonella* infection. Chicks can also be obtained from another source shown to produce chicks that have a reduced possibility of SE contamination. The chicks can then follow a vaccination schedule to prevent vertical SE contamination of the egg product. The vaccination schedule can comprise the administration of specified vaccination sequence using specific types of vaccines. The first administration can be conducted within the first 48 hours of hatching. This first dose can be a USDA-licensed *Salmonella typhimurium* (ST) live attenuated mutant vaccine 211. A second dose of the USDA-licensed ST live attenuated mutant vaccine can be administered to the chicks between 10 and 30 days from hatching 212. These two administrations of ST vaccine can establish intestinal tissue immunity.

The third vaccine administration to the pullets can comprise a dose of USDA-licensed *Salmonella Enteritidis* multi-phage type, inactivated oil emulsion vaccine by the intramuscular route and can be administered when the pullets reach 12 to 14 weeks in age 213. The third vaccination can establish humoral (circulating antibody) immunity. Additional vaccinations can also be administered in response to increased risk of infection. By applying this vaccination schedule, the probability of vertical transfer of SE from hen to egg can be greatly reduced. FDA guidelines and regulations do not include the vaccination of chicks for use in egg production. After following this vaccination schedule, the immature hens can be transferred to egg production farms 214.

Contamination Control

Contamination control methods can also be used to prevent SE contamination from outside sources, including rodents, flies and vermin. Rodent control and the prevention of outside animal access to the facilities can be essential to the prevention of SE contamination of flocks and the eggs produced from those flocks. These animals, especially mice, can harbor *Salmonella*. If allowed to access the feed storage areas or laying houses, these animals can easily contaminate the flocks. Buildings should be sealed and free of entry points. Additionally, curiosity traps can be located throughout the area to monitor for activity of mice. The areas in and surrounding the building can be made free of vegetation and any scrap materials which can provide harborage and opportunity for rodent breeding. An apron of at least two feet of concrete or crushed stone can surround each building to prevent burrowing and to make visible any droppings that are present.

Bait stations can be located at 30-40 foot intervals around the perimeter of houses, feed mills and packing plants. Additional bait stations can be placed at 40 foot intervals in aisles adjacent to the long and eave walls of poultry houses and in the corridors. Bait stations can be placed adjacent to egg conveyers that pass between houses and tamper-proof bait stations can be used within feed mills and packing plants. These bait stations can then be re-baited every week. Of course, all of the rodent control standards mandated by the FDA must also be followed.

In addition to rodent control, a fly control program can also be included. The fly-control program can include: minimizing manure moisture by providing sufficient ventilation, use of beneficial insects, and the application of USDA and EPA approved insecticides in accordance with their labels. The fly population can be monitored and appropriate management of manure can be taken at the time of flock depletion, when placing young flocks, and at times of exceptional climatic conditions.

Finally, entry of vermin and wild birds, can be prevented by the installation of screens over ventilation openings and other such access points. Any other methods known to those skilled in the art to prevent access of animals and other birds to feed sources can also be included as part of the present method.

Biosecurity procedures can be used to prevent of the introduction of contaminants into any of the process areas. The use of biosecurity measures, such as monitoring the introduction of contaminants through contact with people, outside animals, food, and water can be effective in preventing SE contamination of an egg. The biosecurity procedures for the present method of producing a verified enriched egg can be in accordance with the SE-Prevention Program as mandated by the FDA.

The introduction of contaminants can also occur through the products ingested by the flock. Feed cannot contain animal by-products as these by-products can introduce SE contamination. Special precautions, such as sequencing or flushing, can be taken to prevent possible contamination of the feed for use with flocks producing a VESE, if the feed contains by-products. Additionally, the use of surface water supplied to flocks producing VESEs can be restricted. Surface water can be supplied to flocks producing VESEs only after the water has been chlorinated to kill any bacteria. Any water supplied to flocks originating from wells can be tested at least every six months for potability and can be treated to eliminate coliform bacteria present. After the end of a production cycle, the cage houses can be dry cleaned following the procedures as detailed in the FDA SE Guidance Document.

SE Negative Verification

Figure 3:
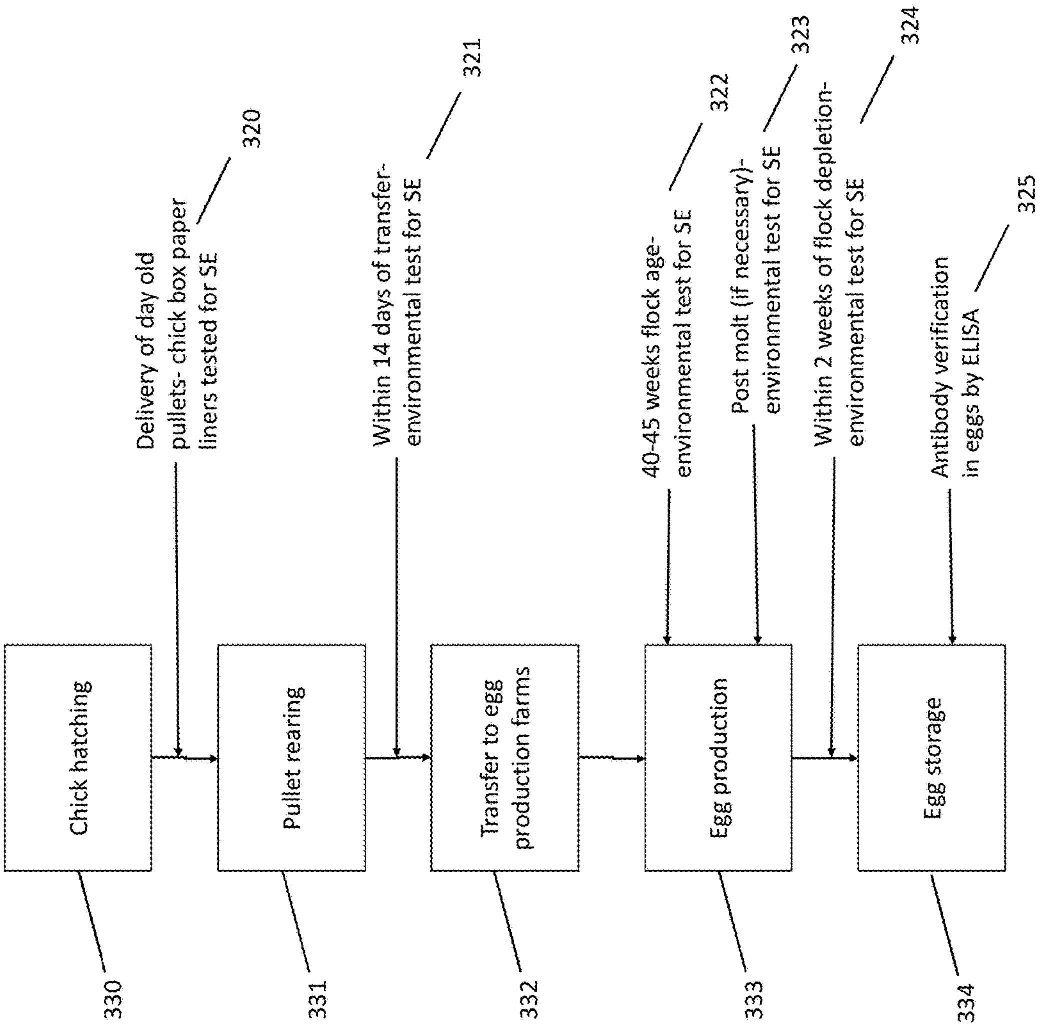
FIG. 3 is a flow chart showing the time periods for SE monitoring for a VESE according to an embodiment.

FIG. 3 is a flow chart showing the time periods for SE monitoring for a VESE according to an embodiment. A verification and monitoring program can also be established to ensure the efficacy of the vaccination schedule, as well as compliance by those rearing the chicks. Environmental tests can be conducted by obtaining samples from day-old chick box liners, approximately 14 weeks pre-transfer, between 40 and 45 weeks, post-molt, and an antibody test can be conducted on eggs obtained from the packing plant. Sample eggs from each flock can also be tested.

The method of sampling and the microbiological procedures used during the testing process can comply with the requirements of the NPIP as administered by the USDA Animal, Plant Health Inspection Services. After the chicks are hatched 330, samples to confirm the absence of *Salmonella* Group-$D_1$ serotypes and SE can be obtained from chick-box paper liners at the time of delivery of day-old pullets 320. The pullets can then be reared 331 and similar samples for these two strains of *Salmonella* can be obtained by the same procedures from the environment of pullets within two weeks of transfer to the laying houses 321. The pullets can then be transferred to egg production farms 332 and egg production can begin 333. Additional similar environmental tests for SE can be conducted between 40 and 45 weeks of age 322, within four weeks of commencing production in the second cycle (if molted) 323, and within two weeks of depletion of flocks at the end of their productive life 324. SE tests can be completed by an accredited laboratory that applies procedures as approved by the FDA. Throughout the egg production time, the eggs can be moved to storage facilities 334 and antibody verification in the eggs can be conducted using an enzyme-linked immunosorbant assay (ELISA) 325.

The FDA *Salmonella* prevention rules only require testing for SE when the pullets are 14-16 weeks old, 40-45 weeks, and 4-6 weeks after each molt. The current industry practice only requires additional testing if an environmental test is positive. In contrast, the present method can require testing in addition to the standard environmental testing and the testing that is statutorily required. Specifically, in the present process all eggs from a flock that yields a positive environmental test can be excluded. Additionally, the present method can include verification that the flock producing the VESE received an effective dosing of SE vaccination.

The vaccination verification step can be a test of the egg yolk from eggs located at the packing plant. At least 18 eggs from each new flock, and then quarterly thereafter, can be obtained from the packing plant. The immune status of the flock can be tested by verifying the antibody levels in the egg yolk through the use of an enzyme-linked immunosorbant assay (ELISA). The presence of sufficient antibodies in the egg yolk can provide an indication of the immune status of the flocks. A positive antibody test can indicate that the immunity of the flock to SE is strong and that the vertical passage of SE to the eggs can be significantly reduced.

Additional testing of environment, final feed and feed ingredient samples, and eggs can be required to be submitted as requested for routine monitoring or special surveillance. Environmental samples can also be obtained during routine or special auditing of facilities.

Figure 4:
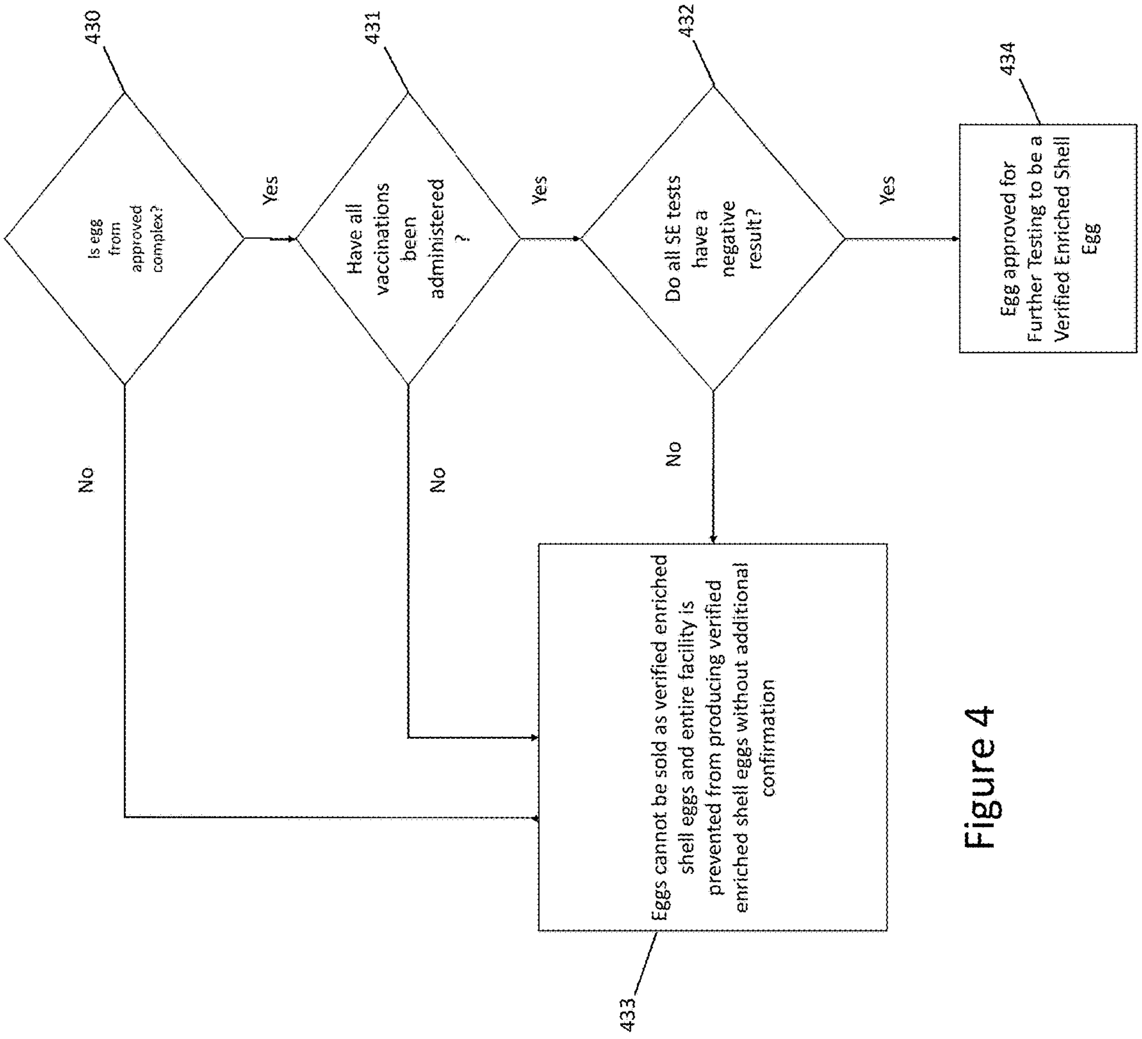
FIG. 4 is a flow chart showing the steps regarding ensuring that an egg is free from SE contamination, which an egg can be required to pass prior to qualifying to be a VESE, according to an embodiment.

FIG. 4 is a flow chart showing the steps necessary to ensure that an egg is free from SE contamination such that the egg can qualify to be categorized as a VESE. The egg can be from an approved complex 430. The flocks producing the egg can receive all vaccinations 431 listed in FIG. 2 and all SE testing as provided in FIG. 3 can be required to be negative 432. If any of the verification tests performed discloses the presence of SE contamination in the flocks, the eggs, or a single egg the flocks can be disqualified from the program and any eggs associated with the flock that are in storage can be destroyed 433. The disqualification and destruction of the possibly contaminated eggs ensures that the final VESEs are free of SE contamination. If a flock passes each of the requirements it can be used to produce VESEs 434.

If an environmental test is positive, the entire facility can be prevented from being able to produce VESEs. The transfer of egg production from the positive test location to a different location at the same facility cannot be permitted without the confirmation that these other location are free from contamination. Additionally, if a subsequent flock at a single facility tests positive for SE or *Salmonella* Group $D_1$ the facility can be eliminated from producing VESEs.

Nutritional Content Control and Verification

Feed Production:

As a part of a method to provide a VESE, procedures and verification processes can be followed to provide an egg that comprises an increased amount of beneficial nutrients and a reduced amount of saturated fat and cholesterol. This nutrient production and verification method can be conducted along with the SE elimination, egg quality and marking procedures to produce a VESE. Additionally, this nutrient production and verification method can be used alone to provide a VESE that can comprise a beneficial balance of nutritional contents.

Many nutrients contained in an egg product can be controlled through the feed mixture that is provided to the laying flock. This feed mixture can be formulated by a qualified nutritionist with suggestions made by the primary breeder of the strain housed. Specifically, the feed mixture can exclude specific undesirable ingredients, in order to reduce the amount of saturated fats, while supplementing other nutrients, which can increase the levels of vitamins E, D, and Omega-3 fatty acids contained in the VESE. Specifically the items included in Table A (in any combination thereof) can be modified in the feed.

TABLE A

| |
|---|
| Animal Fats |
| Supplement Mix comprises Vitamins D and E |
| Increased Flaxseed and/or Canola Oil |

Animal fats can be eliminated from the feed mixture in order reduce saturated fats, the feed supplement mix can comprise Vitamin D and E to increase the amounts of these nutrients, and the amount of flaxseed and/or canola oil can be increased to ensure that the VESE comprises sufficient levels of Omega-3 fatty acids.

A suitable feed mixture can be created by excluding undesirable ingredients that can deteriorate the quality of the eggs laid by a flock. The ingredients to be excluded (in any combination thereof) can include the items listed in Table B.

TABLE B

| |
|---|
| Animal Source Ingredients |
| Recycled Vegetable Products |
| Antibiotics and Other Additives |
| Clay Anti-Caking Agents |
| Cottonseed Meal and Its Derivatives |

In addition to excluding specific ingredients, a suitable feed mixture can also be made to comprise a feed supplement mix that can be formulated to elevate the amount of desired nutrients contained in the VESE.

The feed supplement can comprise:

Crude Protein (min) . . . 4.00%

Crude Fat (min) . . . 3.0%

Crude Fiber (Max.) . . . 12.0%

Selenium (Min.) . . . 60.0 ppm

Manganese (min.) . . . 2.40%

Zinc (Min.) . . . 2.40%

Phytase (*schizosaccharomyces Pombe/Aspergillus Niger*) (Min.) . . . 90 FTU/g.

The feed supplement mix can also comprise a vitamin E supplement having a concentration between 150,000 IUs and 230,000 IUs. If this range of vitamin E is provided in the feed supplement, the vitamin E level in the shell egg can be within 7.5 IUs and 8.5 IUs. A desired (or target) amount of vitamin E within a shell egg can minimally be 3 IUs (10% of Daily Value), which would be considered to be nutritionally significant. Vitamin E has been shown to contribute to improved cellular and body tissue health.

In an embodiment of the current method, a vitamin D supplement can also be included in the feed supplement mix having a concentration of between 8,000,000 IUs and 160,000,000 IUs. This range of vitamin D in the feed supplement can provide a VESE with a vitamin D level from 80 IUs to 160 IUs. The range of content from 40 IUs to 160 IUs of vitamin D (10% to 35% of the Daily Value) would be considered nutritionally significant. Vitamin D can promote beneficial health effects, such as improving the body's utilization of calcium and phosphorus. Vitamin D also plays a role in promoting cell growth, strengthening immune function, and reducing inflammation.

The feed supplement mix can be added to the feed mixture at a rate of approximately 10 lbs/ton. As mentioned above, the feed mixture can also comprise a minimum amount of canola oil and/or flax seed. This parameter can provide the VESE with a minimum amount of Omega-3 fatty acids. In an embodiment, the feed mixture can comprise a minimum of 55 lbs canola oil per ton of feed, or alternatively, a minimum of 30 lbs of whole flaxseed plus 10 lbs of canola oil. Whole flaxseed can be replaced with co-extruded flaxseed at an inclusion that is twice that of whole flaxseed. The following relative inclusion rates can be used according to availability or cost:

| Canola oil (%) | Flax Seed (%) |
|---|---|
| 2.75 | 0.0 |
| 1.9 | 0.5 |
| 1.2 | 1.0 |
| 0.5 minimum | 1.5 |

Having the flexibility to use various ratios of canola oil and flaxseed in the feed mixture can provide greater consistency in the amount of Omega-3 fatty acids contained within the VESE. In an alternate embodiment, additional sources of Omega-3 fatty acids can also be used to supplement, or be used in place of the canola oil and flax seed combinations in the feed supplement mix, including but not limited to, flax oil, chia seeds or soybean oil.

Note that when feeding whole flaxseed, supplemental granite grit can be provided to flocks to facilitate digestion. In an embodiment, the addition of 5 to 50 lbs of ⅛" granite grit to one ton of the first two deliveries of feed mixture to the flock can be sufficient to achieve this purpose. Additionally, flaxseed inclusion can be kept below 5% to prevent it from interfering with the absorption of iodine. Also, canola oil can be added to diets at a level not exceeding 10% of the ration. In an embodiment, flocks can be fed the feed for at least 10 days prior to obtaining any VESEs to ensure that desired nutrient levels are achieved.

Figure 5:
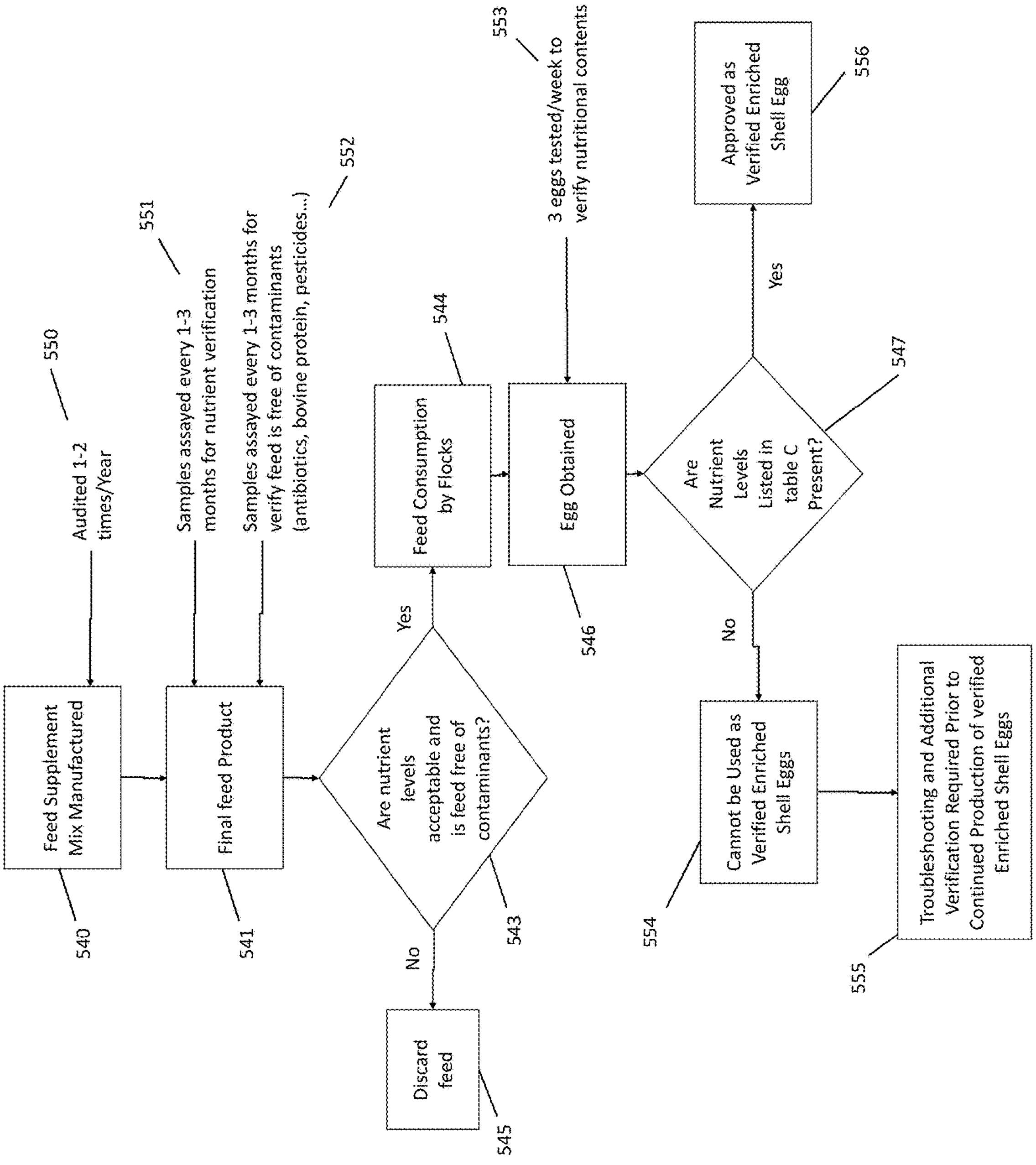
FIG. 5 is a flow chart showing the verification steps to ensure that the proper nutrient levels are present in the VESEs, according to an embodiment.

Feed Verification:

According to an embodiment, an auditing program can be included in the method in order to verify the contents of the feed mixture that is being fed to flocks producing VESEs. FIG. 5 is a flow chart showing the verification steps to ensure that the proper nutrient levels are present in the VESEs.

The manufacturer of the feed supplement can manufacture the feed supplement mix 540. Throughout the manufacturing process the manufacturer can be audited periodically, with the preference of the audit occurring in the range of every 6 months to one year 550. This audit can review documentation relating to the source and purity of ingredients, inventory rotation, procedures to ensure compliance with formulas, and positive identification of batches of product and expiry dates. In an embodiment, inventory levels and conditions of storage can be monitored to ensure proper stock rotation and incorporation in flock diet. By properly monitoring and rotating the inventory levels, prolonged storage can be avoided and age-related deterioration of the potency of ingredients can be prevented.

After the feed supplement mix is manufactured it can be incorporated into the final feed product 541. In addition to testing the feed supplement mix, the final feed product can also be assayed to ensure that the appropriate levels of supplemental nutrients are contained in the feed product being fed to the flocks producing VESEs. Samples to verify the nutritional content of the feed can be obtained every 1-3 months 551. The feed can also be assayed to determine qualitatively if the contents of the feed supplement mix are present in the final feed product. Additionally, according to an embodiment, the final feed products can be assayed every 1-3 months to confirm that the feed is free from antibiotics, protein of bovine-origin, and pesticides 552. If the feed has both acceptable nutrient levels and is free of contaminants including (in any combination thereof) antibiotics, protein if bovine-origin and pesticides 543 the feed can be consumed by flocks 544. If either of these qualifications are not acceptable the feed can be discarded 545.

After the flock has consumed the verified feed an egg can be obtained 546. In an embodiment of the present method, the nutrient levels of eggs obtained from each flock can be assayed weekly 553. In such an assay, three representative eggs can be obtained from each flock every week. To perform the assay, the interior contents of the representative egg samples, comprising the yolk and albumen, can be homogenized and a subsample from the blended egg samples can then be lyophilized and ground into a fine powder. In an embodiment of the present method, subsamples can then be subjected to gas-liquid chromatic analysis to verify the level of vitamin E, vitamin D, saturated fat, and Omega-3 fatty acids. Samples can also be submitted to independent certified analytical laboratories to validate the accuracy of the weekly in-house assays. According to an embodiment, the acceptable ranges (per 50-gram edible interior portion) can be as listed in Table C 547.

TABLE C

| NUTRIENT | ACCEPTABLE RANGE |
|---|---|
| Vitamin E | 7.5 to 9 IU's |
| Vitamin D | 120 to 160 IU's |
| Omega-3 Fatty Acids | 115 to 300 mg |
| Saturated Fat | ≤1.2 g |

Corrective Actions:

According to an embodiment of the present method, if all the nutrients for the tested eggs are within the nutrient levels shown in Table C are present, the egg can be used as a VESE 556. If a nutrient level is not within the desired range, the associated eggs cannot be used as VESEs 554. Additionally, investigations should be conducted to ensure that subsequently produced eggs meet the nutrient standards 555. Specifically, if one or more of the nutrients tested are not within the acceptable ranges, the age of the feed supplement used to create the feed mixture can be checked. According to the present method, the feed supplement should not be older than 90 days, as the quality of the nutrients can deteriorate over time. Additionally, the inclusion rate of the feed supplement within the feed can be assayed. The inclusion rate can be 10 lbs of feed supplement mix per one ton of feed. Lastly, the qualities and quantities of other ingredients comprising the feed mixture can be measured. For example, the quality and age of the canola oil used can be determined. If the oil is oxidized, it could oxidize some of the nutrients in the feed supplement mix, lowering the potency and inclusion of these nutrients into the VESE.

If the final egg product comprises higher than desired amounts of saturated fat, the feed can be checked for presence of animal fat and, if present, its source can be determined and excluded. Additionally, the use of canola oil and flaxseed at the proper amounts can be checked to ensure that they are within the proper percentage of the flock diet. Corrective actions for low Omega-3 levels can include ensuring that the proper amounts of canola and/or flaxseed have been included. Additionally, in an embodiment, the quality of the canola oil can be tested to ensure that lower quality oil, such as soap stock or used frying oil, has not been added to the feed mixture. Such contaminants can lead to substandard amounts of Omega-3 fatty acids in the VESE.

In addition to determining the factors contributing to insufficient or lower quality nutrients in the tested eggs, all eggs produced from the flock, including those eggs that do not meet the nutrient standard, can be flagged within a flock management software system and prevented from being used as VESEs. Once the cause of the non-acceptable results has been determined, the number and source of eggs that must be excluded from the VESEs can also be determined. Only eggs that are associated with eggs that were assayed and passed all nutritional verifications can be VESEs.

Finally, if no source of the decrease in nutritional content of the assayed eggs can be determined, the amounts of the nutrients can be increased in the feed supplement mix. Once the eggs are verified to contain the acceptable levels of nutrients as shown in table C they can be included as VESEs 556.

The nutritional production and verification as described can be performed along with the SE contamination production and verification steps to produce a VESE that can be free of SE contamination, provide high levels of desirable nutrients, and low levels of undesirable nutrients. Additionally, these processes can be performed with egg quality procedures, verification and tracking procedures, and marking procedures to produce a VESE.

Egg Physical Quality Production and Verification

Egg Production:

Additional process controls can be implemented to ensure that the VESE has optimal physical properties. The desirable physical properties that can be controlled by set production processes include albumen height, Haugh unit value, yolk color and shell strength.

The nutritional supplementation can also provide some beneficial physical properties to the VESE. Specifically, the inclusion of vitamin E and vitamin D in the feed supplement mix can contribute to improved and sustained egg quality. The feed supplement mix can also include selenium, iodine, manganese, copper, and zinc, which have been shown to contribute to improved egg quality. These nutrients can be included in the feed supplement mix in the following amounts:

| Nutrient | Amount (per 10 lbs feed supplement mix) |
|---|---|
| Selenium | 225-275 mg |
| Iodine | 2,000-4,000 mg |
| Manganese | 80,000-110,000 mg |
| Copper | 5,000-14,000 mg |
| Zinc | 80,000-110,000 mg |

Management practices within the laying houses and treatment of the eggs can also impact the quality of the VESE. The age of the flock effects the quality of the eggs produced. Flocks producing VESEs typically cannot be older than 65 weeks of age during the first production cycle, or 76 weeks of age for cage-free layers. Molted flocks typically cannot be used more than 25 weeks after reaching 50% production during the second cycle and cannot be over 95 weeks old. Flock cycles may be extended to older ages contingent on satisfactory improvements in hen genetics.

To ensure that the VESE can obtain the increase in quality from the nutritional supplementation, the supplemental feed mix can be fed to the flock for a minimum of 10 days prior to the collection of VESEs for packaging and distribution.

Higher standards of care can protect against possible deterioration in physical qualities of an egg that can occur during storage and transportation. Eggs can be removed from houses at least once every 24 hours for packing inline or storage offline. The eggs can then be transferred to coolers daily. The coolers can be operated at a temperature below 45 degrees F. and at a humidity range from 70% to 85% RH. Egg storage can comply with the strictest requirements set by state or federal guidelines. Eggs can be transported to a packing plant at intervals typically not exceeding 7 days, with a preferable interval of 4 days, which can be more important in the summer months.

The processing plant can also follow requirements to ensure that the VESE has good physical properties. Once the egg reaches the processing plant it can be stored in a cooler that must be maintained at or below a temperature of 45 degrees F. and a relative humidity of 70% to 85% RH, and the storage facility can be free of odors and any evidence of fungal or bacterial contamination. The processing plant can have ventilation sources and proper drainage to prevent condensation and accumulation of water. The eggs can be stored in the cooler for 7 days or less prior to processing. Offline eggs can be stored to equilibrate at room temperature for up to 24 hours after removal from a cooler to prevent thermal cracks during washing.

Washing can occur using an approved egg washing solution in accordance with labeling instructions. The pH value of the solution can be maintained between 10 and 12; the chlorine sanitizer level can range from 100 to 150 ppm and can incorporate a surfactant. The final rinse temperature can range from 130 to 140 degrees F., and can be at least 15 degrees F. greater than the temperature of the wash water.

Once the VESE product is packaged in cartons or cases they can be transferred to pallets and held in a cooler that can have a temperature at or less than 45 degrees F. and a relative humidity between 70% and 85% RH. Transport trailers can be equipped with refrigeration units to maintain a temperature below 45 degrees F. during transit. Inventory can be rotated on a first in, first out basis and inventory turnover can ensure that the VESE is distributed to stores preferably within 5 days of processing and into the hands of the consumers shortly thereafter. High impact cases can be used if the VESE is expected to be transported over 500 miles or handled more than 3 times.

Minimizing the time period from laying to marketing can ensure that the egg quality does not have a long period of time to degrade. Additionally, maintaining proper temperatures in storage can help maintain the internal physical properties of the VESE and the transportation requirements can reduce shell cracking and maintain the external physical characteristics of the egg.

Physical Quality Verification and Corrective Actions:

Verification methods can be applied to ensure that the VESE has high quality internal and external characteristics. In addition to the eggs being subjected to the voluntary USDA grading policies, the VESE can also be required to pass additional verification steps.

Figure 6:
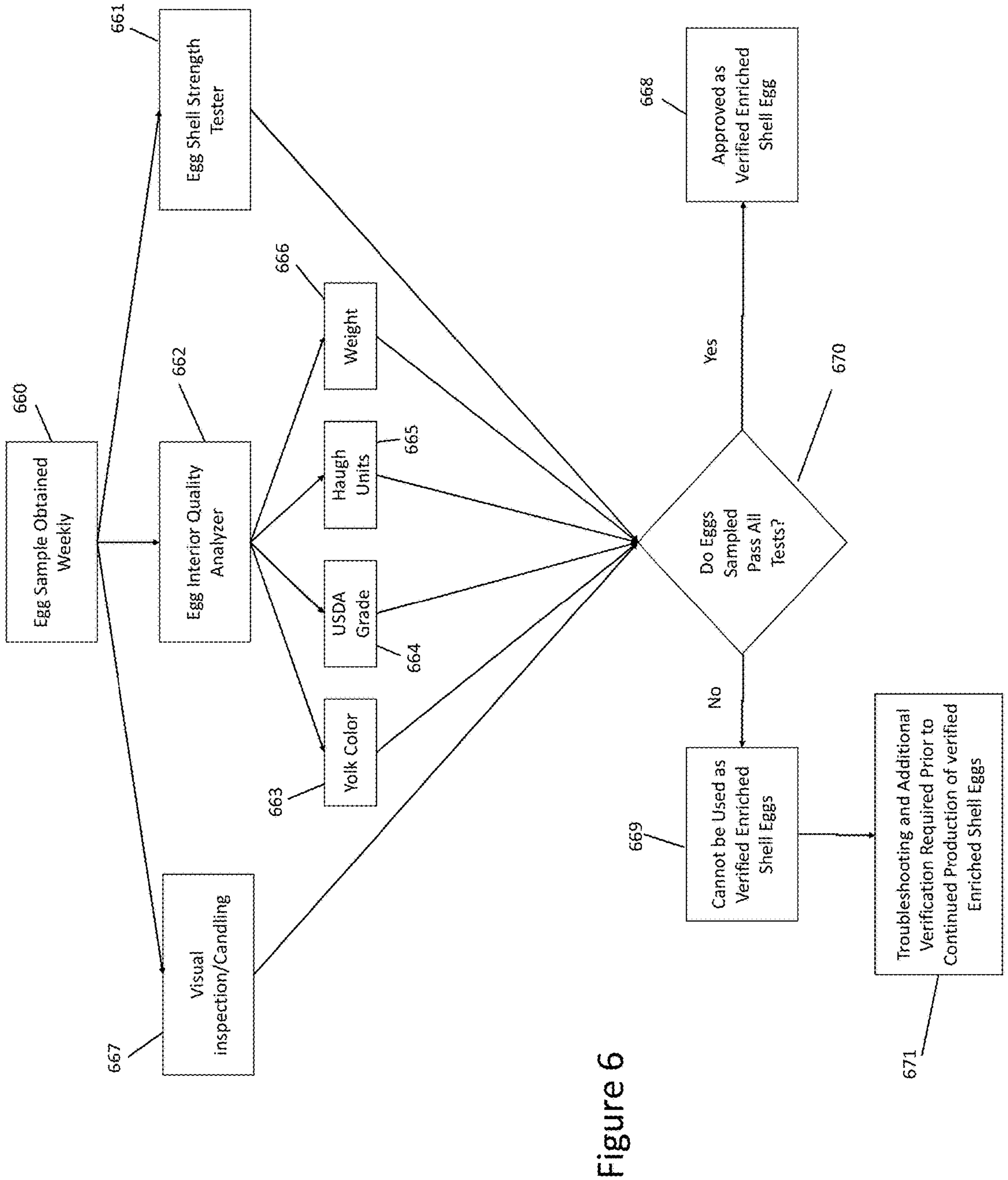
FIG. 6 is a flow chart showing the steps that can be followed to verify the physical characteristics of a VESE, according to an embodiment.

FIG. 6 is a flow chart showing the steps that can be followed to verify the physical characteristics of a VESE. Representative sample eggs can be obtained from each flock weekly 660, preferably three eggs can be obtained, but any number sufficient for performing every verification test is contemplated. These sample eggs can be the same as the samples obtained for nutritional analysis. The shell integrity of the sample egg can be tested by adding a measurable force to the egg and determining the force at which it breaks. Such testing can be done by using an egg shell strength tester 661. Additionally, the internal and external quality of the sample egg can be determined using an egg interior quality analyzer 662. The electronic instrument can determine the yolk color 663, USDA Grade 664, Haugh units 665 and weight 666 of the sample egg. Additionally, visual inspection of the exterior of the shell can be conducted 667.

Candling of the VESE can occur at the processing plant prior to packaging. The operators of the candling booth can be trained to remove unacceptable eggs, including obviously blood-filled eggs and products with defective shells (leakers, windowed, cracked and mottled.) All lights in the candling booth can be functional and ambient light can be reduced to a low level. Additionally, candling operators can be rotated frequently to conduct other functions that are not a strain on the individual's concentration or hand-eye coordination.

The information regarding the different internal and external tests 667, 662 and 661 can be entered into a software system or database and it can be determine if all eggs sampled pass all of the tests 670. The tested eggs can meet minimum standards for each of the tests in order to qualify as VESEs 668. If one of the sample eggs does not meet the minimum standards for any one of the verification tests, the associated eggs can be flagged by a flock management software system and can then be prevented from being used as VESEs 669. Additionally, excessive prevalence of checks, pimpling, abnormal shape or shell color can disqualify the flock. Flocks producing eggs with suboptimal physical characteristics can be prevented from producing VESEs irrespective of the age of the flock. Once a flock has been linked with an egg sample that does not meet all of the standard troubleshooting and additional verification can be required prior to that flock being able to continue production of VESEs 671. This troubleshooting can include verification of the inclusion of the feed supplement mix in the feed consumed by the flocks can be conducted if egg quality does not meet acceptable standards.

Flock Management System

A flock management software system can be used to track each flock producing VESEs. The flock management system can ensure that flocks not meeting the standards to produce VESEs are excluded from the process.

Specifically, the flock management system can comprise software that is accessible by farms housing VESE-producing flocks. The farm can enter the information for a new flock into the software when a new flock is to be used to produce VESEs. The following information can be required for each new flock entered: name, designation (classic, cage free or organic), age and start date, vaccination dates, hen breed, and flock size. Once this information is saved, a new flock is created within the flock management software.

Each month the farm can supply reports to the flock management software within the first seven day of the new month. The monthly report can include the month and year, the current flock size, the current production status, average hen production, average case weight, percent of eggs not qualified to be VESEs (due to cracking, checks or size), average feed consumption (lbs per 100 birds) and any additional comments. The system can then automatically exclude flocks that are not within the required age or do not meet the minimum standards for producing VESEs. Additionally, items that may be a concern, such as variables in feed consumption or egg size can be flagged and investigated further for potential issues.

At the time a flock is added to the flock management system the SE status of the flock can also be entered. This initial status will not change for the flock, but environmental reports can be uploaded into the system. The flock management system can remind the farm of the time period when environmental SE testing is required and prevent the use of flocks that either fail the SE testing or have failed to have data entered about them within the specified time period.

Data for each flock can be entered into the system and be tracked and stored in a database. Specifically, SE environmental test results, the egg internal and external quality results, nutritional content results and antibody verification results (or any combination thereof) can be entered into the system. The system can then determine if any one of these parameters does not conform to the desired standards and provide an alert. Additionally, the system database can store the information for future reference or viewing.

Additionally, yearly certifications can be entered into the flock management system. These certifications can include: American Humane Certification, Humane Farm Animal Care Certification, Organic Certification, Organic System Plan/Verification Document, SQF Safe Quality Food Audit Certificate. The flock management system can exclude flocks from specific programs if any required certificate is not up to date or is missing. The use of the flock management system ensures conformity with the VESE procedures. All methods described herein can be tracked and verified. Specifically, the system and track whether all tests have been passed, or which tests have failed, the date of testing, the age and location of the flocks.

Figure 7A:
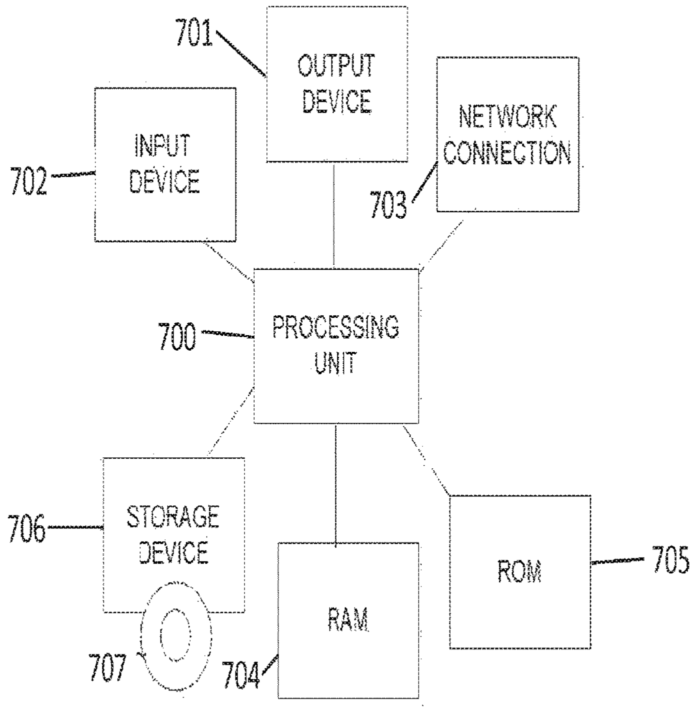
FIG. 7A is a block diagram illustrating hardware that can be used to implement the flock management system described herein, according to an embodiment.

FIG. 7A is a block diagram illustrating hardware that can be used to implement the flock management system described herein, according to an embodiment. The hardware can be, for example, a computer located at the farm or within a laboratory. The hardware can also be a personal computer, located at a location remote from the farm or laboratory and can be located in an office. The hardware can also be any device capable of uploading information, such as a cellular phone, tablet, etc., and the methods described herein can be installed as software (e.g., an app) on the device. The hardware can also be any other type of device, working individually or in conjunction with other devices.

A processing unit 700 (such as a microprocessor and any associated components) is connected to an output device 701 (such as an LCD monitor, touch screen, CRT, etc.) which is used to display to the user any aspect of the method, and an input device 702 (e.g., buttons, a touch screen, a keyboard, mouse, etc.) which can be used to input from the user any information relating to the flock. All methods described herein can be performed by the processing unit 700 by loading and executing respective instructions. The processing unit 700 can also be connected to a network connection 703, which can connect the hardware to a computer communications network such as the Internet, a LAN, WAN, etc. The processing unit 700 is also connected to a RAM 704 and a ROM 705. The processing unit 700 is also connected to a storage device 706 which can be a DVD-drive, CD-ROM, flash memory, etc. Multiple such processing units can also work in collaboration with each other (in a same or different physical location). A non-transitory computer readable storage medium 707 can store a program which can control the electronic device to perform any of the methods described herein and can be read by the storage device 706. The processing unit 700 can also be connected to a laboratory computer or instrument 708 which can provide information regarding the results of the verification processes described herein. All methods described herein can be tracked and if any of the verification processes do not meet the minimum requirements, the system can implement a change in the status of a flock, indicating that the flock is no longer approved to produce VESE. Additionally, when any of the verifications are not met, notification can be presented on the screen and the affected flocks can be prevented from producing VESEs.

While one processing unit is shown, it can be appreciated that one or more such processor can work together (either in a same physical location or in different locations) to combine to implement any of the methods described herein. Programs and/or data required to implement any of the methods/features described herein can all be stored on any non-transitory computer readable storage medium (volatile or non-volatile, such as CD-ROM, RAM, ROM, EPROM, microprocessor cache, etc.)

Figure 7B:
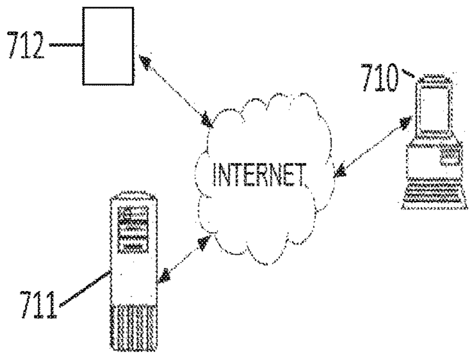
FIG. 7B is a block diagram illustrating an exemplary network configuration to implement a flock management system, according to an embodiment.

FIG. 7B is a block diagram illustrating an exemplary network configuration to implement a flock management system. All the methods described herein can be implemented on an piece of hardware that can have internet access. A user can use a personal computer 710 (e.g., cell phone, tablet, PC, etc.) to connect to a server 711 (which can have the structure illustrated in FIG. 7A) using a computer communications network such as the Internet. The server 711 hosts an online system that determines the whether a flock is eligible for producing VSESs and serves the outcomes to the computer 710 so the computer 710 displays the outcomes to the user. Other users can also access the information hosted by the server 711 simultaneously, such as using a cell phone 712 with wireless internet connectivity. Any number of users connected to the internet can view the information provided from the farm or laboratory at the sever 711.

Figure 8:
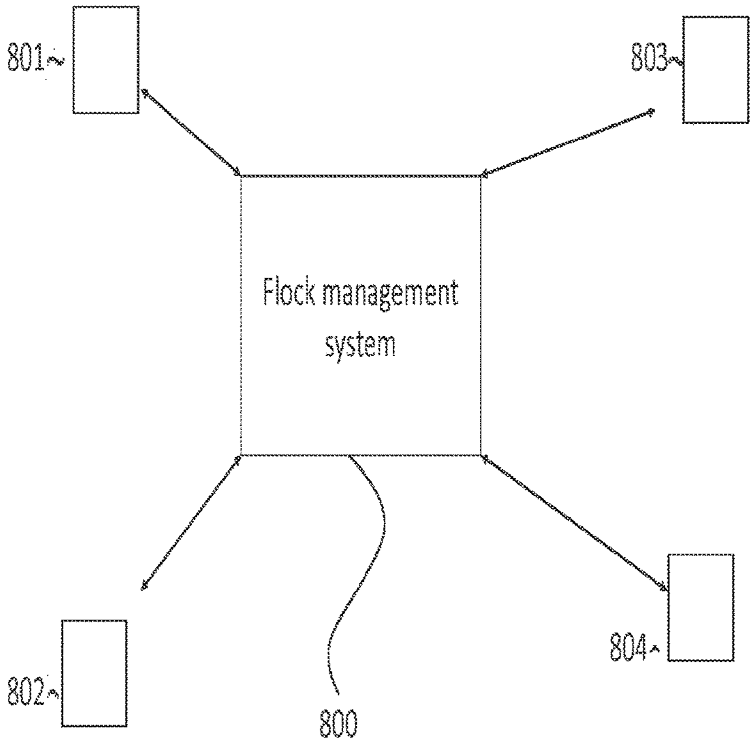
FIG. 8 is a topological diagram showing the configuration of different hardware that can be used to implement a flock management system, according to an embodiment.

FIG. 8 is a topological diagram showing the configuration of different hardware that can be used to implement a flock management system. Hardware, such as a handheld device or computer can be located at various locations that are part of the egg verification process. These devices can be used to add pertinent information to the flock management system 800 so that non-qualified flocks can be prevented from producing VESEs. A first device 801 can be located at the farm. This device can be used to upload data regarding each flocks, as described above, including hatch date, feed consumption and the results of environmental tests. A second device 802 can be located at different location and can be accessible to a second user. Information provided to the system from the first device 801 can be processed in the system and displayed for view at the second device 802. Additional devices can be used to either provide additional data relating to a flock or view information about a flock at a remote location. Specifically, a third device 804 can be located at a laboratory that is analyzing egg quality. The results of this analysis can be entered manually or automatically into the system and associated with a specific flock. All results and data can be entered and stored on the flock management system 800. Finally, a forth device 804 devices can be used to remotely access the information on the system, such that a person, or inspector located at a facility can provide information, or view the existing information in real time, which can allow for a quick response time for non-qualified flocks to be prevented from producing VESEs. Additional devices can also be utilized to provide or view information in the flock management system, with a minimum of one device required for the system to work.

Egg Marking

VESEs can be kept separate from other eggs produced or handled at the same facilities. Special precautions can be taken to segregate eggs from flocks producing VESEs from those producing generic eggs. This can be accomplished by scheduling the sequence of operation of collecting belts and packing for in-line operations. Barriers on in-line conveyers can be used to separate generic eggs from the VESEs. For off-line production, VESEs can be collected daily and can be farm-packed on clean, dry plastic or fiber trays. Racks of pallets used to transport VESEs can be differentiated by using color-coded, bar-coded, or other labeling methods that are readily distinguishable. All racks comprising VESEs can be identified by flock origin and date of production using a color-coded card to maintain a trace back to the farm of origin.

Throughout processing, VESEs can be positively identified and segregated from generic eggs. During the packing process, the packing equipment can operate at a speed that ensures the eggs are dry prior to stamping. Additionally, the packing equipment can orient the eggs such that the larger end is facing up and available for stamping. Each VESE can be stamped with a mark identifying it as a VESE. The stamp can be applied by egg stamping machines that are known in the art of egg production. The rate of speed and ink used can be selected to ensure that the stamp is clearly visible and legible to the consumer.

Verification of the orientation of the eggs and the stamping effectiveness in the packaging can be carried out at a minimum by open carton inspections during the first 30 minutes of operation and 15 minutes following each work break or maintenance period. Continuous open-carton inspections can be preferred, but minimally 1 of every 10 cartons can be checked during this time period. In the event of defects the affected packer can be stopped and repairs and adjustments can be carried out prior to resuming packing. Additionally, 1 packed case of each grade from each packer can be examined during each shift and preferably every 2 hours. Sub-standard product can be reworked.

Each of the production processes and verification methods presented above can be performed with each of the other production processes and verification methods. The combination of all of the production processes and verification methods can result in a VESE that is known to the public to have a minimal possibility of SE contamination, elevated amounts of desirable nutrients, minimal amounts of undesirable nutrients, and good physical properties.

Figure 9:
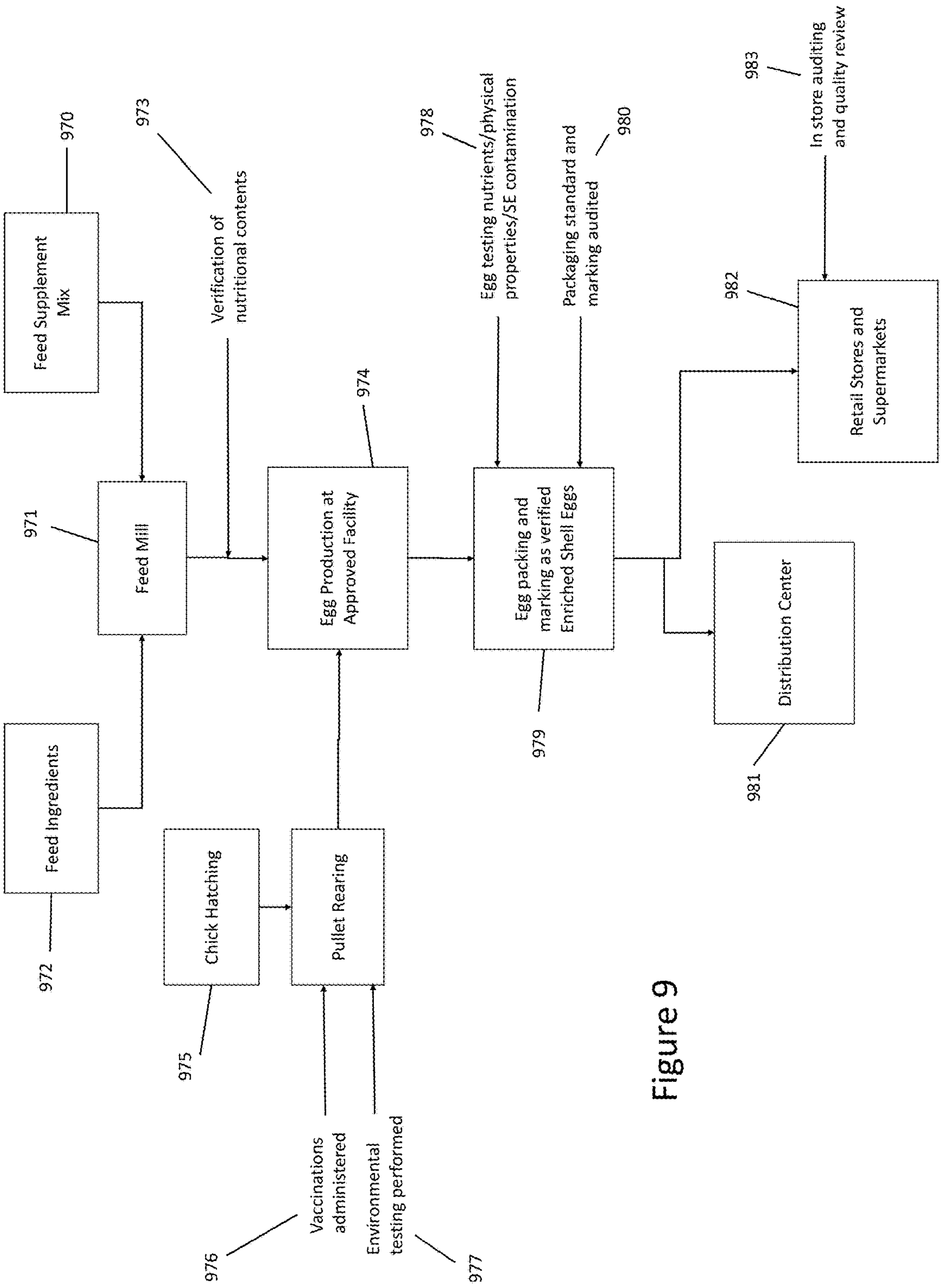
FIG. 9 is a flow chart showing the interaction of each of the individual production and verification steps to produce a VESE, according to an embodiment.

FIG. 9 is a flow chart showing the interaction of each of the individual production and verification steps to produce a VESE. The feed supplement mix can be created at a production plant that is audited regularly. The nutrient content of the supplement mix can be verified before it is sent to the feed mill to be incorporated into the final feed product. The feed mill 971 can combine the feed ingredients 972 with the feed supplement mix 970. After the final feed product is created, it can be tested to ensure proper level of nutrients are present and that it is free of undesirable contents, such as antibiotics and proteins of bovine origin 973. The feed can then be fed to the hens at the egg production facilities 974.

The chicks to be used for egg production can be hatched at facilities operated in accordance with NPIP 975. The chicks can receive the specified vaccines 976 and be transferred to egg production facilities 974. Environmental testing can be performed to ensure that the hens are free of SE contamination 977. Egg from the egg production facilities can be obtained and testing on the eggs can include nutrient verification, physical property verification, and ELISA titer verification that the eggs are free of SE 978. Eggs that pass all tests can be packaged and marked as VESEs 979. The marking and packaging can be visually inspected to meet the specified standards 980. If the packaging and marking is acceptable, the VESEs can be transferred to distribution centers 981 and retail stores 982. The storage at these location can meet minimum standards as set forth above, and auditing and quality reviews of these locations can occur regularly 983.

Although the present production and verification method and resulting egg product therefrom have been described in terms of exemplary embodiments, they are not limited thereto. Rather, the appended claims should be construed broadly, to include other variants and embodiments of the process and product, which may be made by those skilled in the art without departing from the scope and range of equivalents of the present inventive concept.

What is claimed is:

1. A method for producing a verified enriched shell egg comprising:
- providing a chicken from a flock;
- providing a feed supplement mix comprising a vitamin D supplement and a vitamin E supplement;
- mixing the feed supplement mix with a feed mixture comprising canola oil to create a feed product;
- performing an assay to verify that the final feed product is free from antibiotics, proteins from bovine sources, and pesticides;
- feeding the final feed product to the chicken;
- obtaining a first egg from the chicken;
- testing the first egg for an acceptable level of vitamin D, vitamin E, saturated fat and Omega-3 fatty acids; and
- obtaining a second egg from the chicken if the levels of vitamin D, vitamin E, saturated fat and Omega-3 fatty acids in the first egg were within acceptable limits,
- wherein acceptable level of Omega-3 fatty acids is between 115-300 mgs.

2. The method for producing a verified enriched shell egg as described in claim 1 further comprising:
- discarding eggs produced from the flock if the first egg does not meet the acceptable levels of Omega-3 fatty acids.

3. A method for producing a verified enriched shell egg comprising:
- providing a chicken;
- vaccinating the chicken with a *Salmonella typhimurium* live attenuated mutant vaccine when the chicken is less than 48 hours old;
- vaccinating the chicken with the *Salmonella typhimurium* live attenuated mutant vaccine when the chicken is between the ages of 14 days and 21 days;
- vaccinating the chicken with a *Salmonella enteritidis* multi-phage type, inactivated oil emulsion vaccine when the chicken is between the ages of 12 weeks and 14 weeks;
- performing an environmental test for *Salmonella enteritidis* contamination of a chick box liner used to house the chicken;
- performing an environmental test for *Salmonella enteritidis* contamination of a laying house housing the chicken when the chicken is 14 weeks old and when the chicken is 40-45 weeks old;
- providing a feed supplement mix comprising a vitamin D supplement and a vitamin E supplement;
- mixing the feed supplement mix with a feed mixture comprising canola oil to create a feed product;
- performing an assay on the feed product to verify that the final feed product is free from antibiotics, proteins of bovine sources and pesticides;
- feeding the final feed product to the chicken;
- obtaining a first egg from the chicken;
- testing the first egg for vitamin D, vitamin E, saturated fat and Omega-3 fatty acids
- testing the first egg for *Salmonella enteritidis* antibodies; and;

obtaining a second egg from the chicken if the levels of vitamin D, vitamin E, saturated fat and Omega-3 fatty acids in the first egg were within acceptable limits and *Salmonella enteritidis* antibodies were present in the first egg.

4. The method for producing a verified enriched shell egg as described in claim 3 wherein acceptable level of Omega-3 fatty acids is between 115-300 mgs.

5. The method for producing a verified enriched shell egg as described in claim 4 further comprising:

discarding eggs produced from the flock if the first egg does not meet the acceptable levels of Omega-3 fatty acids.

* * * * *